United States Patent [19]
Allen

[11] 4,024,150
[45] May 17, 1977

[54] METHOD OF PREPARING AN N,N'-BIS(P-CYANOPHENYL)-4,4'-BIPYRIDYLIUM SALT

[75] Inventor: John Graham Allen, Runcorn, England

[73] Assignee: Imperial Chemical Industries Limited, London, England

[22] Filed: Oct. 4, 1974

[21] Appl. No.: 512,305

Related U.S. Application Data

[63] Continuation-in-part of Ser. No. 257,082, May 26, 1972, abandoned.

[52] U.S. Cl. .......................... 260/294.9; 260/296 D
[51] Int. Cl.² ...................................... C07D 213/22
[58] Field of Search ................... 260/294.9, 296 D

[56] References Cited

UNITED STATES PATENTS 3,697,528  10/1972  Andrews et al. ............... 260/294.9

OTHER PUBLICATIONS

Klingsberg, "Pyridine and Its Derivatives" part 2 (1961), pp. 58 and 59.

*Primary Examiner*—Henry R. Jiles
*Assistant Examiner*—R. W. Ramsuer
*Attorney, Agent, or Firm*—Cushman, Darby & Cushman

[57] ABSTRACT

Salts of N,N'-bis(p-cyanophenyl)-4,4'-bipyridylium are prepared by contacting an N,N'-bis(2,4-dinitrophenyl)-4,4'-bipyridylium salt with p-cyano-aniline in an inert polar medium.

5 Claims, No Drawings

METHOD OF PREPARING AN N,N'-BIS(P-CYANOPHENYL)-4,4'-BIPYRIDYLIUM SALT

This application is a continuation-in-part of application Ser. No. 257,082 filed May 26, 1972 and now abandoned.

This invention relates to a process for the production of N,N'-bis(p-cyanophenyl)-4,4'-bipyridylium salts, which are useful in the formulation of photosensitive compositions based on water permeable polymers.

The invention provides a method of preparing N,N'-bis-(p-cyanophenyl)-4,4'-bipyridylium salts (hereinafter CPP) which comprises the step of contacting an N,N'-bis(2,4-dinitrophenyl)-4,4'-bipyridylium (hereinafter DNP) salt with p-cyanoaniline in an inert polar, preferably aqueous, medium.

Preferred salts employed according to the invention are halides, particularly the fluorides and chlorides, and alkyl sulphates, particularly lower alkyl ($C_1$ to $C_3$) sulphates, for example methyl and ethyl.

Yield of the product is influenced inter alia by the ratio of the p-cyanoaniline to DNP. Preferably at least four moles of p-cyanoaniline are used per mole of DNP salt, the preferred ratio being 5 to 6 moles to one of DNP salt. The upper limit is not critical, but economics and convenience suggest that no more than about 10 moles should be used.

The medium employed should be one which is inert, i.e. does not react chemically with the reactants or reaction products. The medium employed is one capable of dissolving an ionic material. It should provide a high (e.g. >75% w/w) degree (although not necessarily complete) of solubility of the amine. The solvent is preferably water, optionally mixed with water-miscible polar solvents (having a high dielectric constant e.g. greater than 15). Solvents employed should not tend to bring about separation of ionic and nonionic phases, causing uptake of a substantial proportion of the amine in the non-ionic phase. Examples of water-miscible polar solvents which may be employed in admixture with water are alcohols (e.g. methanol, ethanol, propanol) dimethyl formamide and acetonitrile.

Suitably the amount of water present in the medium is sufficient to dissolve the product salt. The water will usually constitute at least 10%, preferably at least 30, and more preferably at least 50% by volume.

Although the use of non-aqueous inert solvents is not excluded and alcoholic media, for example methanol, ethanol and propanol may be employed, the presence of water in the reaction medium does, we find, increase the yield very markedly and enables shorter reaction times to be employed.

The reaction is conveniently carried out at a temperature at which reflux of the solvent occurs, preferably not higher than about 160° C and preferably the reaction is carried out not lower than about 50° C. It should be noted that not all the p-cyanoaniline need be in solution: part may be in suspension for a time before it is reacted. Reaction under inert atmosphere, for example nitrogen, is preferred.

The reaction time is of the order of ½ to 4 hours. At the end of this time the solution is cooled and some crude CPP may crystallise out.

The remaining liquid can be extracted with a water immiscible organic solvent e.g. chloroform or toluene and more solid recovered by evaporation of the aqueous solution. The solid materials contain CPP, starting materials, intermediates and 2,4-dinitroaniline.

Digestion of the solids in a hot alcohol, preferably ethanol dissolves the unreacted p-cyanoaniline and non-ionic products and assists in converting intermediates to CPP, which is not very soluble in ethanol.

The product CPP can be recrystallised from glacial acetic acid. The crystals from this process still contain acetic acid which may be removed by vacuum drying at at least 80° C. Further purification conveniently comprises one or more of the steps of dissolving the solid in hot water, decolourising with activated charcoal and precipitation from concentrated solution at, say, 60° C by addition to 3 to 5 times its volume of acetone or isobutanol.

CPP has been employed as an electrochromic component is display devices comprising at least two inert electrodes in electrical contact with the compound (usually in aqueous solution). Reduction of the compound by passage of an electric current between the electrodes produced a colouration resulting from the production of coloured radical ions.

The electrodes employed are chemically inert to the electrolyte with which they are in contact, and may be of any suitable material, e.g. metals such as gold, and platinum, electrically conducting glasses or glass or other support material having an electrically conductive inert surface, for example a thin metallic film.

The device can be open circuited, in which case the colour remains stable for several hours. Reversal of the potential produces bleaching, the speed of bleaching being influenced by the positive current applied.

The invention is further illustrated by the following detailed description of a preparation. The preparation of DNP is also described.

Apparatus: (all flame proof)

Reactor: 20 liter QVF flask fitted with an air powered stirrer, total reflux and distillation condensers, charging port, nitrogen bleed and bottom run-off facility.

Heating: 20 liter electric mantle, thermostatically controlled by temperature controller connected to a thermocouple placed between the outer wall of the reaction flask and the mantle.

Preparation of N,N'-bis(2,4-dinitrophenyl)-4,4'-bipyridylium chloride (DNP)

4,4'-bipyridyl; 1560 gm.
1-chloro-2,4-dinitrobenzene; 4500 gm.
methanol (AR grade) solvent; 14 liters.

The reactor was charged with the 1-chloro-2,4-dinitrobenzene (4500 gm) methanol (10 liters), stirred under an atmosphere of nitrogen and heated to gentle reflux. A solution containing 4,4'-bipyridyl (1560 gm) in methanol (4 lites) was added continuously in a thin stream over a period of 5 hours. Reflux conditions were maintained for a further 30 hours before solid product was observed. Total reflux time at this stage was 70 hours. The reaction mixture was cooled to room temperature over a period of 6.5 hours by means of air jets from an annular collar around the reaction vessel. Filtration yielded an orange-yellow crystalline product. The filtrate was returned to the reactor and the solid obtained was washed thoroughly with acetone until washings were colourless, and then dried at 90° C under vacuum. Yield = 1120 gm.

The filtrate was heated to reflux conditions for a further 24 hours when a further crop of 520 gms of product were obtained by filtration.

At this stage the distillation take-off condenser was fitted to the reactor, the filtrate returned to the reactor and reduced in volume by distillation to 3 liters (methanol) over a period of 24 hours. After a further period of 24 hours at reflux, a third crop of product was isolated, 1040 gms.

Total yield = 2.7 Kg, % yield = 48.1% m.pt. of bulked crops 1 and 2 and 3 = 220°–223° C

Preparation of
N,N'-bis(p-cyanophenyl)-4,4'-dipyridylium dichloride
(CPP)

DNP; 1683 gm (3 moles).
p-cyanoaniline; 1770 gm (15 moles).
water as solvent; 12.5 liters.

Reaction apparatus was the same as that used in the synthesis of DNP described above.

The reactor was charged with distilled water (7.5 liters) and heated to 80° C. p-Cyanoaniline (1770 gm) was added whilst stirred under an atmosphere of nitrogen to produce a dispersion of p-cyanoaniline melt in an aqueous solution of p-cyanoaniline. The mixture, was heated to reflux temperature and stirred vigorously whilst a solution containing DNP (1683 gm) is hot distilled water (5 liters) was added over a period of 30 minutes. Reflux conditions were maintained for a further period of 1 hour, and the reaction mixture was then extracted with chloroform (11 liters in all) by shaking the two phases and removing the lower chloroform phase. The extracted deep red coloured aqueous solution was returned to the reactor vessel and reduced in volume to 4 liters by distillation, and then evaporated to dryness in a rotary evaporator. The solid (1) was found to contain CPP and was extracted with water (50°–70° C). The aqueous solutions obtained were reduced to dryness as described above, and the solids from aqueous solutions were bulked.

At this stage the solid was a deep purple red colour and contained a mixture of CPP, the intermediates, some p-cyanoaniline and 2,4-dinitroaniline. The crude product was digested in boiling ethanol (2 liters) which completes the reaction of the intermediates and removes p-cyanoaniline and some 2,4-dinitroaniline. The CPP is only slightly soluble in hot ethanol. The ethanolic solution was cooled to 40° C and filtered. The solid was washed with cold ethanol until washings were pale yellow, and then dried at 60° C under vacuum. The product obtained was recrystallised from glacial acetic acid (sufficient to ensure complete solubility of solid at boiling point). The product of recrystallisation is a pale yellow crystalline solid (needles) which contains acetic acid of crystallisation. Vacuum drying at 80° C and further drying in a fluid-bed drier at 80° C removed acetic acid to leave a pale yellow microcrystalline powder m.p. 230° C.

Yield = 1075 g, % yield = 83.2%.

What we claim is:

1. A method of preparing an N,N'-bis(p-cyanophenyl)-4,4'-bipyridylium salt which comprises contacting a N,N'-bis(2,4-dinitrophenyl)-4,4'-bipyridilium salt with p-cyanoaniline in an inert aqueous polar solvent medium containing at least about 50% water by volume at a temperature of about 160° C or less at which reflux of the solvent occurs.

2. A method according to claim 1, in which the salt is a halide or an alkyl sulphate.

3. A method according to claim 1, in which the mole ratio is between 5 and 6 of p-cyanoaniline to 1 of DNP.

4. A method according to claim 1, in which the medium comprises water together with another inert polar liquid medium.

5. A method according to claim 1 in which the medium is water.

* * * * *

UNITED STATES PATENT OFFICE
CERTIFICATE OF CORRECTION

PATENT NO. : 4,024,150

DATED : May 17, 1977

INVENTOR(S) : John Graham Allen

It is certified that error appears in the above-identified patent and that said Letters Patent are hereby corrected as shown below:

On the front page format, after paragraph "[21]"

insert: --[30] Foreign Application Priority Data

June 2, 1971  Great Britain........18535/71--

Signed and Sealed this

Twenty-ninth Day of November 1977

[SEAL]

Attest:

RUTH C. MASON
Attesting Officer

LUTRELLE F. PARKER
Acting Commissioner of Patents and Trademarks